United States Patent [19]

Ogawa et al.

[11] 3,954,412

[45] May 4, 1976

[54] TEST STRIP FOR PHENYLKETONE BODIES

[75] Inventors: Yasunao Ogawa, Ikeda; Yukio Yonetani, Nara, both of Japan

[73] Assignee: Shionogi & Co., Ltd., Osaka, Japan

[22] Filed: June 17, 1974

[21] Appl. No.: 480,308

[30] Foreign Application Priority Data

Sept. 18, 1973 Japan.............................. 48-105291

[52] U.S. Cl. .......................... 23/253 TP; 23/230 B; 252/408
[51] Int. Cl.² ........................................ G01N 33/16
[58] Field of Search ................... 23/230 B, 253 TP; 252/408

[56] References Cited
UNITED STATES PATENTS

| | | | |
|---|---|---|---|
| 3,048,475 | 8/1962 | Rupe | 23/230 B |
| 3,418,079 | 12/1968 | Rey et al. | 23/253 TP |
| 3,511,611 | 5/1970 | Rush | 23/230 B |
| 3,598,704 | 8/1971 | Dahlqvist | 23/253 TP X |

OTHER PUBLICATIONS

Welcher, "The Analytical Uses of EDTA," Van Nostrand Co. Inc., N.J., 1958, p. 191.
Henry, "Clinical Chemistry Principles & Techniques," Harper & Row, N.Y., 1964, pp. 334–339.
Martell et al., "Chemistry of the Metal Chelate Comp.," Prentice–Hall Inc., N.J., 1956, pp. 517–523, 534–540.

*Primary Examiner*—Morris O. Wolk
*Assistant Examiner*—Arnold Turk
*Attorney, Agent, or Firm*—Wenderoth, Lind & Ponack

[57] ABSTRACT

A test strip for the detection of phenylketone bodies in the body fluids, especially in the urine, comprising an absorbing material, a ferric salt and an iron-chelating agent. The test strip is useful in early diagnosis of phenylketonuria, inborn disorder of phenylalanine metabolism.

3 Claims, No Drawings

TEST STRIP FOR PHENYLKETONE BODIES

This invention relates to a test strip for the detection of phenylketone bodies in the body fluids and to a composition therefor. More particularly, the present invention relates to a test strip for the detection of phenylketone bodies in the body fluids, especially in the urine, comprising an absorbing material, a ferric salt and an iron-chelating agent and to a composition therefor comprising a ferric salt and an iron-chelating agent.

The presence of phenylketone bodies such as phenylpyruvic acid in the body fluids, especially in the urine, is indicative of phenylketonuria which is an inborn disorder of phenylalanine metabolism in the living bodies. Such serious metabolic disease is causal for mental disorders, mental decline, decreased pigmentation, skin diseases, etc. Normal metabolism of phenylalanine to tyrosine is observed in normal newly-born infants. However, since patients with phenylketoneia lack phenylalanine hydroxylase, phenylketone bodies are accumulated in the living bodies, and excreted in the urine in a large amount. Thus, detection of phenylketone bodies such as phenylpyruvic acid in the body fluids (e.g. urine, serum, plasma) provide a diagnosis of phenylketonuria. Since phenylketonuria can be recovered by limiting the uptake of phenylalanine in a diet, early diagnosis of such disease is required.

It is known that a test strip containing as an active component ferric chloride alone or ferric ammonium sulfate alone can be used for the diagnosis of phenylketonuria, but such test strip is unstable and its sensitivity to phenylketone bodies is not high. Japanese Pat. publication No. 14246/1970 discloses a diagnostic composition for phenylketonuria, comprising a ferric salt, an organic acid and a phosphate complexing agent. Also, as a commercially available test paper used for such detection are exemplified a test paper comprising ferric ammonium sulfate and sodium cyclamate, and a test paper comprising ferric ammonium sulfate, magnesium sulfate and boric acid. However, when these test papers are contacted with a diaper moist with urine, the diaper becomes colored and dirty with the reagent contained in the test paper, and the formed color of the test paper is not uniform and prone to fade rapidly. To the contrary, the test strips of the invention for phenylketonuria do not possess such drawbacks mentioned above, and they show various advantageous features as following: (1) the result of the test is reliable, (2) semiquantitative analysis is possible, (3) the test strip can detect phenylketone bodies in the urine at a concentration of more than 10 mg/100 ml, (4) distinct, stable, and uniform color [yellow (normal)—blueish green (abnormal)] appears immediately, and the determination can be quickly made, (5) the color formed by the test does not fade rapidly, (6) the detection of phenylketone bodies is even possible on a diaper moist with urine without making it dirty.

Thus, the test strips of the invention can be used easily, quickly, and exactly in early diagnosis of phenylketone bodies in the body fluids, especially in the urine. The compositions of the invention show these beneficial features as discussed above.

The test strips for phenylketonuria and the compositions therefore will be hereinafter described in detail.

To prepare the test strip according to the present invention, a ferric salt and an iron-chelating agent are first dissolved in a suitable solvent to give a yellowish solution. An absorbing material such as paper, cloth, or a stick of wood is dipped in this solution at about room temperature, and then the dipped absorbing material is dried in the air or at a temperature of from room temperature to 50°C, to give the desired test strip. As an alternative method, the test strip of the invention can be prepared by dipping an absorbing material in a solution containing all the necessary components. It is to be noted that the order of addition of the said components is of no particular importance. A surfactant such as polyethyleneglycol 4000 may be added to the impregnating solution for the stabilization of the active components. Although the solution itself containing the active components can be applied to the detection of phenylketone bodies, a test strip can be conveniently used, in view of the preservation, stability, and handling.

As the ferric salt are mentioned organic or inorganic ferric salts, such as ferric chloride, ferric bromide, ferric fluoride, ferric sulfate, ferric ammonium sulfate, ferric nitrate, ferric phosphate, and ferric oxalate. The iron-chelating agent can be a compound capable of forming a chelate compound with iron and of not inhibiting the color reaction. Such chelating agents are preferably ethylenediaminetetraacetic acid, nitrilotriacetic acid, 1,2-cyclohexanediaminetetraacetic acid, glycoletherdiaminetetraacetic acid, diethylenetriaminepentaacetic acid, triethanolamine, diethanolamine, diacetylmonooxime, and inorganic salts thereof (e.g. alkali metal salts). Among these compounds, it is especially preferable to use ethylenediaminetetraacetic acid and an alkali metal salt thereof (e.g. sodium salt, potassium salt). These iron-chelating agents coordinate with a ferric ion together with phenylketone bodies to give a colored chelate compound which contributes much to the stabilization of the ferric ion. Thus, it is considered that distinct and stable color is formed without the undesirable formation of ferric hydroxide as a precipitate. Also, the chelating agent can mask various metal ions in the body fluids which affect undesirably the color reaction. As a result, highly stable color with strong intensity is formed in the color reaction.

The solvents used in the production of the impregnating solution include, for example, water, organic solvents (e.g. methanol, ethanol, acetone, having a low boiling point) and a mixture thereof. When an aqueous organic solvent is employed, the reagent in such a solvent soaks smoothly and homogeneously into the absorbing material, thus giving a uniform color in the color reaction. In addition, the drying process for the production of the test strips is simplified in such a case.

The ferric salt is generally used in the form of a solution at a concentration of 1–20 percent, and the iron-chelating agent may be used in the form of a solution having a concentration of about 0.1–10 percent. The optimum concentration of both solutions is each approximately 5 percent.

The absorbing material to be dipped in a solution containing the ferric salt and the iron-chelating agent can be a sheet of paper, a piece of cloth and a stick of wood. Typical examples of the kind of paper are filter paper, blotting paper, absorbent paper (e.g. silica gel paper, alumina paper), ion-exchange cellulose paper (e.g. phosphonomethyl cellulose paper, sulfoethyl cellulose paper, phospho cellulose paper, guanidoethyl cellulose paper, diethylaminoethyl cellulose paper, aminoethyl cellulose paper, Ecteola cellulose paper, p-aminobenzyl cellulose paper, polyethyleneimine cellulose paper obtained by treating cellulose with epichlorhydrin and triethanolamine), ion-exchange Sephadex paper, and ion-exchange resin paper. Other absorbing materials having the same property may be used as well. Among such absorbing material, ion-exchange cellulose papers, particularly diethylaminoethyl cellulose paper, can be preferably employed. The shape of the absorbing material is not particularly limited, though it is usually used in a strip form.

The solution itself containing the active ingredients may be used to detect phenylketone bodies by adding it to a specimen of body fluids such as urine, plasma or serum, whereby a detectable color change results. However, from the point of view of handling, stability, and preservation in practical use, the composition is advantageously used in the form of a solid preparation, rather than the impregnating solution itself. Solid preparations such as tablets, granules, pills, or powders containing the necessary components can be prepared in a conventional manner. In the production of such preparations, suitable additives (e.g. excipient, disintegrating agent, dispersing agent, binder) may be added without changing the basis of the present invention. The color change is detectable only by dissolving such solid preparation in the body fluids containing phenylketone bodies. Also, the color reaction may be effected in such a manner that a tablet containing a ferric salt and a tablet containing an iron-chelating agent, normally separately packed, are combined in a specimen of body fluids when used.

Usually, the test strip of the present invention is used by dipping it in a test sample or by impregnating a test sample into the test strip, whereby detectable color change results. Phenylketonuria can be detected even by using a diaper moist with newborn infant's urine by contacting the test strip with the said diaper. When plasma or serum is employed as a test sample, the same application is possible using the test strip of the invention. The test strip of the invention may be, if desired, used in a more convenient form such as, for example, being held on a plastic sheet.

The following examples are given only to illustrate the embodiments of the present invention, and it is to be construed that the scope of the invention is not limited by the examples given, many equivalent variations of which are possible.

EXAMPLE 1

Ferric chloride (1 g) and ethylenediaminetetraacetic acid (1 g) were dissolved in water (20 ml) to give a clear yellow solution. A piece (5 × 15 cm) of diethylaminoethyl cellulose paper DE-81 (Whatman Co.) was dipped in the above solution for one minute, and then the excess reagent was removed from the paper with a filter paper. The strip was dried in the air or under reduced pressure, held on a plastic sheet, and cut into a suitable size of pieces to give the desired test strip.

When the test strip was tested using urine samples containing $\beta$-phenylpyruvic acid at a concentration of 10, 20, 50, 100, and 200 mg/100 ml, the strip changed color from clear yellow to green, blue, and finally bluenish green as the concentration of $\beta$-phenylpyruvic acid increased. The formed color of the strip did not fade for 5–30 minutes when the test was carried out using the urine sample at a concentration of more than 10 mg/100 ml of $\beta$-phenylpyruvic acid. The color of the test strip itself was clear yellow in the absence of $\beta$-phenylpyruvic acid.

EXAMPLE 2

Using silica gel paper M3F 8860 (Carl Chleicher & Chull Co.) in place of diethylaminoethyl cellulose paper, the same procedure as described in EXAMPLE 1 was carried out to give a test strip for the detection of phenylketone bodies in the urine. The test strip thus obtained showed the same sensitivity to $\beta$-phenylpyruvic acid with that of the strip obtained in EXAMPLE 1.

EXAMPLE 3

Using ferric sulfate (1 g) in place of ferric chloride, the same procedure as described in EXAMPLE 1 was carried out to give a phenylketonuria test strip.

EXAMPLE 4

Glycoletherdiaminetetraacetic acid (1.2 g) and ferric chloride (1 g) were dissolved in water (20 ml) to give a clear yellowish solution. A piece (5 × 6 cm) of diethylaminoethyl cellulose paper SG-81 (Whatman Co.) was dipped in this solution and the paper was dried in the air to give a phenylketonuria test strip. The sensitivity of the test strip to phenylketone bodies was the same with that of the test strip obtained in EXAMPLE 1.

Using nitrilotriacetic acid, 1,2-cyclohexanediaminetetraacetic acid, diethylenetriaminepentaacetic acid, triethanolamine and diacetylmonooxime in place of glycoletherdiaminetetraacetic acid, the same procedure as above was followed to give corresponding phenylketonuria test strips.

EXAMPLE 5

Using filter paper (Toyo filter paper No. 131) in place of diethylaminoethyl cellulose paper, the same procedure as described in EXAMPLE 1 was carried out to give a phenylketonuria test strip.

EXAMPLE 6

Ferric chloride (1 g) and ethylenediaminetetraacetic acid disodium salt (1 g) were dissolved in a 10 percent aqueous ethanol (20 ml), and the procedure of EXAMPLE 1 was followed to give a phenylketonuria test strip.

EXAMPLE 7

Using ferric ammonium sulfate (1.3 g) in place of ferric chloride, the same procedure as described in EXAMPLE 1 was carried out to give a phenylketonuria test strip.

EXAMPLE 8

Ferric chloride (1 g), ethylenediaminetetraacetic acid (1 g) and polyethyleneglycol 4000 (2 g) were dissolved in water (20 ml), and then the procedure of EXAMPLE 1 was followed to give the desired test strip.

We claim:
1. A test strip for the detection of phenylketone bodies which comprises diethylaminoethyl cellulose paper, a ferric salt selected from the group consisting of ferric chloride, ferric bromide, ferric fluoride, ferric sulfate, ferric ammonium sulfate, ferric nitrate, ferric phosphate, ferric oxalate and ferric citrate, and an alkali metal salt of ethylenediaminetetraacetic acid.

2. A test strip for the detection of phenylketone bodies according to claim 1 wherein the diethylaminoethyl cellulose paper is impregnated with a solution of the ferric salt at a concentration of from 1 to 20 grams per 100 ml. of solution and ethylenediaminetetraacetic acid disodium salt at a concentration of from 0.1 to 10 grams per 100 ml of solution.

3. A test strip for the detection of phenylketone bodies according to claim 1 wherein the diethylaminoethyl cellulose paper is impregnated with a solution of the ferric salt at a concentration of 5 grams per 100 ml. of solution and the ethylenediaminetetraacetic acid salt at a concentration of 5 grams per 100 ml. of solution.

* * * * *